(12) United States Patent
Gräter

(10) Patent No.: US 7,951,423 B2
(45) Date of Patent: May 31, 2011

(54) SURFACE-STRUCTURED SUBSTRATE AND PRODUCTION THEREOF

(75) Inventor: Stefan Gräter, Esslingen (DE)

(73) Assignee: Max-Planck-Gesellschaft zur Fördenrung der Wissenschaften e.V., Munich (DE)

( * ) Notice: Subject to any disclaimer, the term of this patent is extended or adjusted under 35 U.S.C. 154(b) by 809 days.

(21) Appl. No.: 11/662,319

(22) PCT Filed: Sep. 12, 2005

(86) PCT No.: PCT/EP2005/009787
§ 371 (c)(1),
(2), (4) Date: Oct. 15, 2007

(87) PCT Pub. No.: WO2006/027274
PCT Pub. Date: Mar. 16, 2006

(65) Prior Publication Data
US 2008/0124535 A1    May 29, 2008

(30) Foreign Application Priority Data

Sep. 10, 2004   (DE) .................. 10 2004 043 908

(51) Int. Cl.
*B05D 5/00*    (2006.01)
(52) U.S. Cl. ........ 427/256; 427/270; 427/271; 427/364; 977/887; 977/890; 977/891; 977/892
(58) Field of Classification Search ................. 427/256, 427/364, 270, 271; 977/887, 890–892
See application file for complete search history.

(56) References Cited

U.S. PATENT DOCUMENTS

| 6,472,802 B1 * | 10/2002 | Choi et al. ................. 313/309 |
| 6,590,056 B2 * | 7/2003 | Won et al. .................... 528/25 |
| 2003/0070569 A1 * | 4/2003 | Bulthaup et al. ............ 101/127 |
| 2003/0133963 A1 | 7/2003 | Hubbell et al. |

FOREIGN PATENT DOCUMENTS

DE    197 47 813 A1    5/1999
(Continued)

OTHER PUBLICATIONS

Geyer, W., Statement concerning prior art (2001) {unpublished doctoral dissertation, University of Heidelberg Germany)}.

*Primary Examiner* — Shamim Ahmed
(74) *Attorney, Agent, or Firm* — Drinker Biddle & Reath LLP

(57) ABSTRACT

The invention relates to a method for production of a surface-structured substrate, comprising the steps: (i) production of a first substrate, nanostructured with inorganic nanoclusters on at least one surface, (ii) application of a substrate material for a second substrate, different from the first material to the nanostructured surface of the first substrate as obtained in step (i) and (iii) separation of the first substrate from the second substrate of step (ii), including the inorganic nanoclusters to give a second substrate nanostructured with the nanoclusters. The invention further relates to a surface-structured substrate obtained by said method and the use of the surface-structured substrate for application to a stent or implant material for the adhesion of cells, viruses and/or bacteria and the serum-free culture of cells, for example, for skin replacement and, furthermore, all applications of said substrate in which biological systems can be imitated, modified, examined or quantified by the structured application of biologically-active molecules and the application thereof in optical or electronic components and chemical and biological sensor systems.

42 Claims, 1 Drawing Sheet

FOREIGN PATENT DOCUMENTS

| | | |
|---|---|---|
| DE | 197 47 815 A1 | 5/1999 |
| DE | 197 47 816 A1 | 5/1999 |
| DE | 198 43 411 A1 | 3/2000 |
| DE | 199 52 018 C1 | 8/2001 |
| WO | WO 99/21652 A3 | 5/1999 |
| WO | WO 01/31402 * | 3/2001 |

* cited by examiner

– 1 –

SURFACE-STRUCTURED SUBSTRATE AND PRODUCTION THEREOF

FIELD

The present invention relates to surface-structured substrates comprising ordered surface structures in the nanometer range as well as to a method for producing these substrates with surface structuring in the nanometer range.

BACKGROUND

Periodically and aperiodically microstructured surfaces of a few micrometers to a few nanometers are used for a plurality of applications, especially electronic and optical components as well as sensors and in microtechnology. The production of such microstructured surfaces takes place by using known lithographic techniques suitably selected in accordance with the type of microstructure desired. Thus, e.g., structures in the nanometer range can be produced with electron-beam lithography and ion-beam lithography, and corresponding systems are commercially available. Furthermore, atomic-beam lithography allows large-surface periodic line patterns and different two-dimensional periodic structures to be produced by controlling the interactions of atomic beams with light masks.

However, since these methods have the disadvantage that they are not economically justifiable and/or supply no periodic structures in the nanometer range and/or can only be controlled by physical parameters and therefore require very expensive apparatuses, the so-called micellar block copolymer nanolithography was developed with which nanostructured surfaces with a periodicity in the lower nanometer range between 10 and 170 nm can be produced. The micellar block copolymer nanolithography method is described in detail in the following patents and patent applications: DE 199 52 018, DE 197 47 813, DE 297 47 815 and DE 197 47 816.

Template effects play an important part in micellar block copolymer nanolithography. This includes the setting of auxiliary structures that control the growth, structure and arrangement of the system built on them. Such templates are, e.g., block copolymers and graft copolymers that associate in suitable solvents to micellar core shell systems as well as highly branched dendritic molecules with a core shell structure. These core shell structures serve to localize inorganic precursors from which inorganic particles with a controlled size can be deposited that are spatially separated from each other by the polymeric casing. It is advantageous here that the core shell systems or micelles can be applied as highly ordered monofilms on different substrates by simple deposition procedures such as spin casting or dip coating. The organic matrix is subsequently removed without residue by a gas-plasma process or by pyrolysis as a result of which inorganic nanoparticles are fixed on the substrate in the arrangement in which they were positioned by the organic template. The size of the inorganic nanoparticles is determined by the weighed portion of a determined inorganic precursor compound and the lateral distance between the particles through the structure, especially by the molecular weight of the organic matrix. As a result, particle sizes of Au, Ag, Pt, Pd, Ni, Co, Fe and Ti particles as well as their oxides and alloys between 1 and 20 nm can be deposit in ordered patterns, the patterns having a periodicity corresponding to the spherical core shell system between 10 and 170 nm.

A prerequisite for the above-described micellar block copolymer nanolithography method is that the substrates consist of materials or material mixtures that withstand without damage the gas-plasma process or pyrolysis process for removing the organic matrix. Therefore, customarily noble metals, oxidic glasses, monocrystalline or multicrystalline substrates, semiconductors, metals with or without passivated surface, insulators or in general substrates with a high resistance to subsequent etching procedures are used as substrates. However, organic substrates and a plurality of inorganic substrates are to be excluded on account of their instability in the gas-plasma process or pyrolysis process for use in the block copolymer nanolithography method. Moreover, substrates are excluded whose surface is not level enough to permit a regular self-organization of the polymeric micelles. The coating of membranes that are a few nanometers thick can also not be realized technically with this method.

This is disadvantageous in as far as in particular organic polymeric substrates as well as the inorganic substrates that can not be used for the block copolymer nanolithography method have a great practical and economic significance for the production of, e.g., conductor paths in the manufacture of chips, in the cultivation of cells, bacteria and viruses as well as for the use as implants.

For example, work is being carried out with a large number of cells and cell cultures for practical and economical viewpoints with culture dishes consisting of plastic or special polymers. They are used, e.g., to multiply cells, differentiate cells or to generate tissue in general. However, the nanostructure was previously not able to be transferred to polymeric surfaces and therefore could not be previously used for the adjustment of adhesion-mediated cellular function.

Furthermore, the use of known substrates of metals, glasses monocrystalline or multicrystalline substrates and semiconductors has the disadvantage that they have great strength that can not be adjusted as desired. However, there is a demand for structured surfaces that are soft and flexible and can be applied, e.g., in the form of a foil on objects such as implants or stent materials and thus can provide these objects with a structured surface. Furthermore, the strength of the surfaces plays a part for the differentiation of cells growing on them. In addition, the chemical nature of the surface between the produced structures, that was previously sharply limited, is of great significance for a plurality of applications in biology, optics, sensor engineering and electronics.

SUMMARY

The present invention therefore has the basic task of making available a method for the nanostructuring of substrate surfaces that previously were not able to be structured or could only be structured with great difficulty.

This task is solved with a method for the production of a surface-structured substrate, comprising the steps:

(i) Production of a first substrate that is nanostructured on at least one surface with inorganic nanoclusters, (ii) Application of a substrate material for a second substrate different from the first substrate material on the nanostructured surface of the first substrate, which surface was obtained in step (i), and (iii) Separation of the first substrate from the second substrate from step (ii), including the inorganic nanoclusters, as a result of which a second substrate nanostructured with nanoclusters is obtained.

According to a preferred embodiment a hardenable substrate material is used for the second substrate material in above step (ii), the hardenable substrate material being selected from an organic cross-linkable or non-cross-linkable polymer, a resin, an organic polymerizable and/or cross-linkable oligomer and from an organic polymerizable polymer precursor or mixtures thereof, and hardened. This preferred embodiment is accordingly a method for the production of a polymeric surface-structured substrate, comprising the steps:
(a) Production of a first substrate that is nanostructured on at least one surface with inorganic nanoclusters,
(b) Application of a hardenable substrate material for a second substrate different from the first substrate material on the nanostructured surface of the first substrate, which surface was obtained in step (a), the hardenable substrate material being selected from an organic cross-linkable or non-cross-linkable polymer, a resin, an organic polymerizable and/or cross-linkable oligomer and from an organic polymerizable polymer pre-cursor or mixtures thereof,
(c) Hardening of the substrate material for the second substrate and
(d) Separation of the first substrate from the second substrate obtained in step (c), including the inorganic nanoclusters, which yields a second substrate nanostructured with nanoclusters.

According to another preferred embodiment the second substrate materials that can be used in step (ii) are applied onto the first substrate by thermal evaporation, electron beam evaporation, sputtering or electrochemical deposition.

In the following the individual steps of the method for the production of a surface-structured substrate of the present invention are explained in detail.

In step (i) or (a) a surface nanostructured with inorganic nanoclusters is produced.

The lithography methods known in the state of the art can be used to produce such nanostructured surfaces. The production with the micellar block copolymer nanolithography method with which nanostructured surfaces can be produced in a simple and economic manner is preferred (see DE 199 52 018, DE 197 47 813, DE 297 47 815 and DE 197 47 816.

If the nanostructured surface is produced by a lithography method known in the state of the art the first substrate used consists of a material that is customarily used in this lithography method. In the case of the micellar block copolymer nanolithography method the following substrate materials that can be used are to be named in particular: noble metals, oxidic glasses, monocrystalline or multicrystalline substrates, semiconductors, metals with or without passivated surface, insulators or in general substrates with a high resistance to subsequent etching procedures. They are preferably Pt, Au, GaAs, $Al_xGaAs$, Si, $SiO_2$, Ge, $Si_xN_y$, $Si_xGaAs$, InP, InPsi, GaInAsP, glass, graphite, diamond, mica, $SrTiO_3$ as well as their doped modifications.

It is also possible that the first substrate consists of a polymeric material. Such a nanostructured polymeric substrate can be obtained by the method of the present invention described here. The substrate obtainable in the method of the present application in step (d) can thus be used itself again as a first substrate in step (i) or (a). Any polymers can be used as polymeric material. The following can be named by way of example as especially well-suited polymeric materials: polystyrene, epoxide resins, polydimethylsiloxane (PDMS) and polyethyleneglycoldiacrylates (PEG-DA). A first substrate of polystyrene is especially preferred.

In the above embodiment, in which the second substrate materials that can be used in step (ii) are applied by thermal evaporation, electron beam evaporation, sputtering or electrolytic deposition onto the first substrate, a first substrate of a polymeric material is preferably used, as is indicated above.

The inorganic nanoclusters produced in step (i) or (a) are in particular oxygen-resistant noble metals such as Au, Pt, Pd or oxides such as, e.g., semiconductive oxides such as $TiO_2$, or magnetic particles such as, e.g., certain modifications of $Fe_2O_3$. Furthermore, clusters from metallic mixed systems such as $Au/Fe_2O_3$, $AuCoO$, $Au/CO_3O_4$, $Au/ZnO$, $Au/TiO_2$, $Au/ZrO_2$, $Au/Al_2O_3$, $Au/In_2O_3$, $Pd/Al_2O_3$, $Pd/ZrO_2$, $Pt/Al_2O_3$ and Pt/graphite are also conceivable. The inorganic nanoclusters from Au are preferred.

The clusters applied on the first substrate in step (i) are not limited in their form and can be present as points, lines, surfaces or any other forms. The clusters preferably have a size of 1 nm to 300 μm, especially preferably 1 nm to 150 μm and even more preferably 1 nm to 20 μm. In the case of punctiform clusters, "size of the clusters" signifies the diameter. In the case of lines "size of the clusters" signifies the line width, wherein the length of the lines can be as desired. In the case of cluster surfaces the "cluster size" is a measure for the surface of the cluster.

The obtained structures that are produced on the first substrate preferably have orders of magnitude from 1 nm to 300 μm. In the case of ordered structures they have periodicities 1 nm to 300 μm. As regards a cellular adhesion on a surface-structured substrate an order of magnitude or periodicity from 5 nm to 100 μm is especially preferred. An order of magnitude or periodicity from 5 nm to 100 nm is even more preferred and quite especially preferably 5 nm to 20 nm. An order of magnitude of 5 to 500 nm can be produced, e.g., by the micellar block copolymer nanolithography method. Larger structures can be produced, e.g., by known photolithographic methods.

In step (b) of the method for producing a polymeric surface-structured substrate of the present invention a hardenable material for a second substrate is applied onto the structured surface of the first substrate obtained in step (a). The hardenable material for the second substrate is selected from an organic or inorganic polymer, a resin, an organic polymerizable or cross-linkable oligomer, a cross-linkable polymer and an organic polymerizable polymer precursor. Polystyrene, epoxide resins, polydimethylsiloxane (PDMS), polyethyleneglycoldiacrylates (PEG-DA), e.g., PEG-DA 500, PEG-DA 4000 and PEG-DA 8000, and polyphosphazenes with very different molecular weights can be named as special examples for the hardenable second substrate material.

A special embodiment provides collagens, hyaluronic acid, fibronectin, vitronectin and other natural polymers as hardenable polymer that can be used in step (b).

For electronic applications organic and inorganic conductive and semiconductive polymers are of particular interest, e.g., poly(4,4-dioctylcyclopentadithiophenes).

The hardenable material for the second substrate is preferably applied uniformly with the desired thickness in the form of a liquid or as solution by a coating method customary in the state of the art. For example, polystyrene, poly(4,4-dioctylcyclopentadithiophenes) and polyphosphazenes are applied in solution and PDMS and epoxide resins in a liquid state by a spin centrifugation method onto the first carrier material. PEG-diacrylate is preferably dripped on in solution under protective gas.

It is also possible to additionally provide the second substrate from step (b) with an inorganic carrier layer on the side opposite the first substrate. The inorganic carrier layer can be produced from any inorganic material, preferably from a conductive inorganic material, and consists, e.g., of silicon, zinc oxide, gold, carbon. The inorganic carrier layer can be applied onto the second substrate depending on the inorganic material by known methods such as, e.g., by thermal evaporation, electron beam evaporation, sputtering, electrochemical deposition or as a solid with a smooth surface. It is preferred in this embodiment that that the second substrate has a thickness of only 1 to 20 nm after the hardening in step (c). This can bring it about that the nanoclusters, e.g., gold clusters, applied on the first substrate are embedded in the second substrate in such a manner that they simultaneously make contact with the inorganic carrier layer and are therefore suitable for the production of nanoelectrodes.

In step (c) the hardenable material is hardened for the second substrate. The method for hardening the second substrate material is selected depending on the nature of the substrate material. Thus, e.g., polystyrene and polyphosphazenes, which can be applied as solutions, are heartened by a slow evaporation of the solvent. PDMS and epoxide resins are thermally polymerized or cross-linked and harden as a result thereof. PEG diacrylates are photochemically polymerized and hardened in this manner.

After the hardening the second substrate preferably has a thickness of 1 nm to a few cm and a thickness of 10 nm to 100 cm is especially preferred. With regard to an application of the polymeric surface-structured substrate as foil the second substrate according to step (c) preferably has a thickness of 10 nm to 1 cm, especially preferably 100 nm to 1 mm.

In the embodiment in which the second substrate materials that can be used in step (ii) are applied onto the first substrate by thermal evaporation, electron beam evaporation, sputtering or electrochemical deposition, these usable second substrate materials are conductors or semiconductors preferably selected from Si, C, zinc oxide, Cr, indium oxide, Cu, indium arsenide, gallium arsenide and hexadecafluorophthalo-cyanin (F16CuPc), or materials that can be used for optically relevant coatings such as aluminum oxide, calcium fluoride and magnesium fluoride. For example, an F16CuPc layer can be applied using a microwave generator under the following conditions: temperature: 125° C., pressure: $2 \times 6^{-5}$ torr, treatment time: 100 sec. A Cr layer approximately 50 nm thick can be obtained, e.g., by sputtering. To this end the work is performed with an acceleration voltage of 60 mA and an argon pressure of $1 \times 10^{-5}$ torr. As in the case of the hardenable second substrate material described above the layers produced in this manner also preferably have a thickness of 10 nm to 1 cm, especially preferably 100 nm to 1 mm.

In step (iii) or (d) of the method for the production of a surface-structured substrate or polymeric surface-structured substrate the first substrate is separated from the second substrate applied in step (ii) or from the second substrate, including the nanoclusters, hardened in step (c), which yields a second substrate structured with inorganic nanoclusters in the nanometer range, the nanoclusters being transferred onto the second substrate with the same pattern that the nanoclusters had on the first substrate. The separation takes place in a suitable method either mechanically or by a separating agent that is suitably selected as a function of the nature of the first substrate material and taking into consideration the nature of the second substrate material. Care is to be taken that the separating agent used is selected in such a manner that the first substrate is attacked by the separating agent, e.g., by dissolving, but inversely, the second substrate is as stable and insensitive as possible to this separating agent. Thus, e.g., a first substrate consisting of glass or silicon dioxide can be removed with hydrofluoric acid (e.g., 25%) if the second substrate consists of polystyrene, epoxide resin, polydimethylsiloxane (PDMS), polyethyleneglycol-diacrylate (PEG-DA) or phosphazene. In the case of polystyrene as the first substrate, e.g., toluene can be used as a suitable separating means if the second substrate consists of PEG-DA or PDMS.

The size of the substrate obtained in step (iii) or (d) or of the polymeric substrate with structured surface can be as desired and can be between 100 $nm^2$ and several meters, in accordance with the desired usage. A size of 1 $mm^2$ to 100 $cm^2$ is preferred.

According to a preferred embodiment of the method of the pre-sent invention a step of immobilizing a binding molecule, preferably selected from propanethiol, mercaptopolyethylene-glycolacrylate, cysteamine with acryloylchloride, polyethyleneglycoldithiol, alkylthioglycolate and amino-1-alkylthiol can be carried out between step (i) and step (ii) or step (a) and step (b). "Alkyl" designates a straight or branched, saturated or unsaturated hydrocarbon with 1 to 24 carbon atoms, preferably 4 to 18 carbon atoms, especially preferably 6 to 12 carbon atoms. Amino-1-undecanethiol and allyl-mercaptoacetate have proven to be especially advantageous. The binding molecule should be selected in such a manner that it can be bound specifically to the inorganic nanoclusters and bonds chemically or electrostatically to the second substrate but does not adhere to the first substrate.

The immobilization of the binding molecules takes place with known methods. For example, the binding of propanethiol to gold clusters can take place in the gas phase and the other thiols named above are bound in solution within a reaction time of approximately 12 h to gold clusters.

A better binding of the inorganic nanoclusters in or on the second substrate is achieved by the binding molecules.

In an especially advantageous embodiment cells can be used as binding molecules. In this case the adhesion proteins of the cell bind as a function of the nanostructure on the first substrate only to certain nanoclusters. This can bring it about that after the separation of the first substrate only such nanoclusters remain on the second substrate that are bound to the adhesion proteins of the cell. In this manner important recognitions about the adhesion behavior of cells on nanostructured surfaces can be obtained.

According to a further preferred embodiment a passivation of the areas surrounding the nanoclusters can be carried out following step (iii) or (d) in order to achieve a targeted interaction of, e.g., cells or other biomolecules with the inorganic nanoclusters. Such a passivation by polyethylene-glycol is described, e.g., in US Patent Application 2003/0133963 A1 by J. A. Hubbell. A further possibility for passivation consists in the production of hydroxyl groups on the surfaces of polystyrene substrates or PDMS substrates by an oxygen plasma. Then a molecular PEG monolayer with strong protein-repellent properties can be produced on these hydroxyl groups by binding (3-triethoxysilyl-propyl)-carbamic acid(methoxy-polyethyleneglycol)esters. Moreover, it is known that polystyrene surfaces can be passivated in oxygen plasma with bovine serum albumin (BSA) against protein interactions and cellular adhesion. In order to prevent the non-specific binding of BSA to the area of the structure that should not be passivated, this area must first be protected with another specifically binding substance. Thus, gold clusters can be protected, e.g., with PEG thiols that are bound after a plasma activation of the surface. The binding of the thiol to the gold can be destroyed again in an iodine atmosphere. After the non-specific binding of the BSA to the polystyrene the PEG can then be washed off (see the doctoral dissertation of Wolfgang Geyer, University of Heidelberg, May 4, 2001).

After step (iii) or (d) of the separation of the first substrate and, if necessary, after the above-described passivation, a step of biofunctionalizing the inorganic nanoclusters can be carried out. "Biofunctionalization" designates a step in which specific molecules are applied on the nanostructured clusters in order to functionalize them for certain biological applications. All proteins, protein sequences and other molecules that are biologically interesting can be understood thereunder. These molecules can be adhered to the nano-clusters directly or via different binding molecules. A cyclic RGD peptide with thiol anchor can be bound, e.g., to the gold clusters after the passivation step. The gold clusters can be functionalized in this manner for the specific binding of integrins, a cellular adhesion protein. Another example is the binding of molecular motors such as kinesin or myosin.

According to a further preferred embodiment the substrate material applied in step (b) can be functionalized before or after the hardening with heterobifunctional molecules for the binding of further molecules. The heterobifunctional molecule is constructed in such a manner that it has at least two different functional groups. At least one of these functional groups is such that it can bind to the hardenable material of the second substrate while the chemical functionality of the other functional group(s) remains preserved even after the binding. For example, 2-carboxyethylacrylate, propenethiol and 2-aminoethylmethacrylate are suitable for this. Thus, e.g., a biofunctionalization of the remaining substrate surface can be carried out with any biologically interesting molecules in addition to the biofunctionalization of the nanostructure. In this connection growth factors such as EGF, NGF and TGF as well as cellular adhesion proteins and/or peptides such as fibronectin, RGD and catherines as well as extracellular signal molecules such as vasopressin, interferon, insulin are especially interesting here. Molecules of different types can be fixed adjacent to each other in an ordered manner with such a functionalization, so that they enter into a regulated interaction with each other. For example, a PEG hydrogel into which carboxyl groups are bound during the polymerization can be activated with the growth factor EGF while in addition the nanostructures are functionalized as described above with RGD for cell binding, which can be used, e.g., for serum-free cell cultures. Another example is the geometric arrangement of viral spike proteins on the nanostructures with a functionalization of the hydrogel with cellular growth factors.

Another advantageous embodiment is the use of three-dimensional first substrates. This three-dimensional first substrate is entirely or partially nanostructured on the surface. In step (b) this substrate is entirely or partially embedded in the hardenable material and dissolved out in step (d) so that a three-dimensional structure nanostructured on the surface is obtained. The three-dimensional first substrate can have any three-dimensional form, e.g., a fibrous, spherical or lens-shaped form. For example, the three-dimensional first substrate can be a glass fiber with a diameter of 5 µm to 300 µm whose surfaces are coated with the above-named method with a nanostructure of gold clusters. Colloids coated with gold points are also conceivable. The gold points are activated by the immobilization of cysteamine and acryloylchloride and cast into PEG-DA. The glass fibers can be dissolved out in step (d) with hydrofluoric acid or separated mechanically. Specific activation for the binding of certain cells makes possible a use as nerve canal or stent.

DETAILED DESCRIPTION

Figure 1:
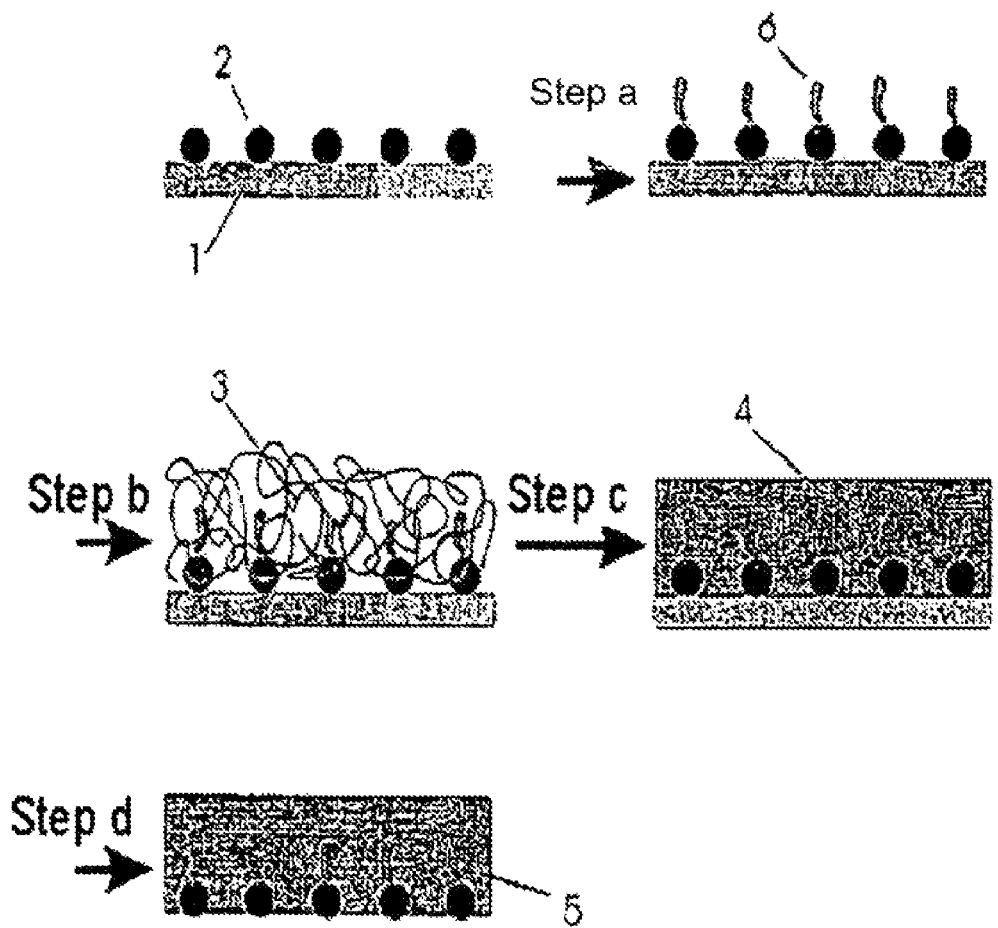
FIG. 1 is a schematic showing a method for the production of a polymeric surface-structured substrate of the present invention in accordance with a preferred embodiment.

The above-described method of the present invention is explained in detail in the following with reference made to FIG. 1.

As is shown in FIG. 1, at first inorganic nanoclusters 2 are applied in a nanostructured manner in a step (a) onto a surface of a first substrate 1. Binding molecules 6 are subsequently immobilized on this nanostructure. Then, in the following step (b) a hardenable substrate material 3 for a second substrate is applied onto the nanostructured surface of first substrate 1. The hardenable substrate material 3 for a second substrate is subsequently hardened in step (c), as a result of which the second substrate 4 is obtained. In step (d) the first substrate 1 is then separated from the second substrate 4 and the nanoclusters 2 including the binding molecules 6, as a result of which a second substrate 5 nanostructured with nanoclusters is obtained.

According to an alternative embodiment the above task of the invention is also solved by a method for the production of a polymeric surface-structured substrate, comprising the steps:

(a') Taking up a polymer in a suitable solvent under formation of a dissolved core shell polymer system, (b') Charging of at least one part of the cores of the core shell polymer system with one or more, same or different metal compounds that form nanoclusters, (c') Application of the core shell polymer system obtained in step (b') as a film onto at least one side of a substrate in such a manner that the core shell polymer system is arranged in a regular structure in the film, and (d') Partial removal of the polymer of the core shell polymer system applied on the substrate in step (c'), as a result of which the nanoclusters are no longer completely surrounded by the polymer, and (e') Separation of the substrate from the film obtained in step (d'), as a result of which a polymeric film nanostructured with nanoclusters is obtained.

Steps (a') to (c') correspond to the procedure usually used in micellar block copolymer nanolithography. Details for carrying out these steps are found in publications DE 199 52 018, DE 197 47 813, DE 297 47 815 and DE 197 47 816.

For example, macromolecular amphiphiles are to be understood under the expression "core shell polymer system" that associate in aqueous or organic solution and can form well-defined spherical or rod-shaped micelles, lamellae, vesicles or complex aggregates. Therefore, according to the invention those systems generally designated as host/guest systems are also included in which a molecular hollow space or molecular inner space, that is, the polymer core, produced by the polymer used (host compound) can be charged or complexed with a host compound, that is, the metal compound used.

The polymer used in accordance with the invention, that constructs the core shell polymer system, is preferably selected from block copolymers, graft copolymers, microarm star polymers, star polymers with different arms, dendritic polymers, microgel particles, star block polymers, block star polymers and core shell latex polymers.

The polymer polystyrene-b-polyethylene oxide, polystyrene-poly(2-vinyl pyridine), polystyrene-poly(4-vinyl pyridine) or a mixture thereof is more preferred. However, the polystyrene block in them can also be replaced by other non-polar polymers such as, e.g., polyisoprene, polybutadiene, polymethylmethacrylate or other polymethacrylates. The second or polar block in such a two-block copolymer can be one that enters an interaction that is as strong as possible with the metal compound used. Examples for this are polyacrylic acid, polymethacrylic acid, amino-substituted polystyrenes, polyacrylates or polymethacrylates, amino-substituted polydienes, polyethylene imines, saponified polyoxazolines or hydrogenated polyacrylic nitrile. The first block can also be constructed from a polar polymer but with the condition that the metal compound is then selected in such a manner that it interacts mainly, that is, selectively, with the second polar block.

Typically, the previously named polymer systems are dissolved in a selective solvent such as, e.g., toluene in an amount of approximately $10^3$ to 100 mg/ml. preferably approximately 5 mg/ml. After approximately 12 hours the solution is compounded with one or several metal compounds in step (b') of the method in accordance with the invention and vigorously agitated for 24 hours in order to charge at least a part of polymer cores formed by the core shell polymer system with the metal compound(s).

The metal compounds are the same as those for the above-described metal clusters. Au or an Au compound is also preferred in this alternative embodiment.

In step (c') of the method in accordance with the invention the application of the film in monolayers or multilayers on at least one side of a substrate is preferably carried out by dipping, casting, spin centrifugation methods or by adsorption from dilute solution. The application in monolayers or multilayers is more preferably carried out by dipping methods in dilute solution. In a preferred embodiment the metal compound(s) contained in the polymer core is/are transferred before step (c') by chemical treatment and/or by energy-rich radiation, e.g., UV light, X-ray radiation or electron bombardment in solution or in the film into the metal or a metal oxide.

The following can be named in particular as usable substrate materials for the substrate in the case of the micellar block copolymer nanolithography method: noble metals, oxidic glasses, monocrystalline or multicrystalline substrates, semiconductors, metals with or without passivated surface, insulators or in general substrates with a high resistance to the following etching procedures. Pt, Au, GaAs, $Al_xGaAs$, Si, $SiO_2$, Ge, $Si_xN_y$, $Si_xGaAs$, InP, InPsi, GaInAsP, glass, graphite, diamond, mica, $SrTiO_3$ as well as their doped modifications.

The films contained in step (c'), that is, macroscopically covering films, are achieved, e.g., by the defined drawing of the substrate from the solution at speeds between, e.g., 0.001 mm/min and 2 m/min. The polymer cores charged with the metal compound are separated essentially intact thereby under formation of a regular structure in the film.

In step (d') of the method in accordance with the invention the film together with the substrate at least partially covered by the film is subjected to a reactive ion etching method, an ion sputtering method or a wet-chemical method or a combination thereof. The structures deposited on the substrate surface serve as a mask transferred by etching techniques into the corresponding substrate, wherein only a part of the film applied on the substrate is removed without a residue at the desired position or the desired area, and where the regular structure produced by the core shell polymer system is converted into a relief structure of the substrate on account of and as a function of the type of the charge of the polymer cores as well as of the duration of the ion etching method and/or of the ion sputtering method and/or of the wet-chemical method. An ion etching with argon, ozone, oxygen and their mixtures is preferably carried out, an argon-ion sputtering is more preferable. The expression "partial removal" means that the nanoclusters are no longer completely surrounded by the polymer after the partial removal. Preferably 20 to 80% of the surface of the inorganic clusters remains surrounded by the polymer. More preferably, an area of 30 to 70% of the surface of the clusters is covered with polymer after the partial removal of the applied film, even more preferably 40 to 60% and most preferably 50%.

The thickness of the film applied in step (c') is preferably 1 nm to a few cm, especially 10 nm to 100 cm, especially preferably 10 nm to 1 cm, even more preferably 100 nm to 1 mm.

Step (e') of the separation of the substrate from the film contained in step (d') takes place in the same manner as described for step (d) according to claim 1.

The polymeric substrate with nanostructured surfaces obtainable from the above-described method in accordance with the invention can be applied in particular on implant materials and stent materials and be used as culture substrates for cells, bacteria and viruses, as nutrient bottoms for differentiation experiments on stem cells and nutrient bottoms for tissue. Soft polymeric substrates play a part in particular for neuronal growth. Furthermore, they can also be used for electronic components and for moistening/moisture removal and against the contamination of objects. An example thereof is the use in a serum-free cell culture for the generation of skin replacement. Furthermore, substrates with nanostructured surfaces and obtainable with the method in accordance with the invention are important for very different usages in which biological systems are imitated, manipulated, examined and quantified via a precise arrangement of biologically active molecules, e.g., the imitation of interactions of viruses or pollen with cells, the manipulation of cell differentiation to desired phenotypes and the binding of molecular motors in order to examine and quantify their activities. Furthermore, they can also be used for electronic and optical components, the use of semi-conductive substrates being especially interesting, as well as biological or chemical sensors and be used for moistening/moisture removal and against the contamination of objects.

In addition, a particular advantage of the present invention is that the binding receptors and the proteins in the cell can be arranged and positioned via the geometry and chemical and physical nature of the surface on which a cell can adhere in such a manner that the function of the cell, e.g., the activity of biochemical signal paths, gene expression and the synthesis of certain cellular proteins can be purposefully controlled by this.

The present invention is explained in detail in the following by examples.

Example 1

Transfer of Gold Structures from a Glass Surface onto Polystyrene

An exsiccator with the glass substrate with the gold structure to be transferred is evacuated and connected to a Schlenk flask in which a few μl propenethiol are present. The propenethiol evaporated in this manner acts for 12 hours on the substrate surface.

After aeration and rinsing of the substrate in the nitrogen countercurrent a polystyrene/toluene solution (25 mg/ml) is dripped onto the substrate surface through a 0.2 μm syringe filter (ca. 5 μl/cm$^2$).

After 6 hours drying time at room temperature the polystyrene is hardened in an oven for 1 hour at 60° C. The substrate is placed with the side covered with the polystyrene facing up into a 12% hydrofluoric acid solution. After a few seconds the polystyrene film floats, is rinsed with MQ water and blown dry with nitrogen.

Example 2

Transfer of Gold Structures from a Glass Surface onto Poly-Ethyleneglycol

The glass substrate with the gold structures to be transferred is placed for 12 hours in a 5% solution of PEG-dithiol in DMF.

After rinsing in MQ water a solution of 300 mg PEG-diacrylate (PEG-DA), 0.15 mg photoinitiator (Irgacure 2959) and 300 ml water is applied (ca. 5 µl/cm$^2$) in the nitrogen countercurrent.

The matter is irradiated under nitrogen for 45 min with a UV lamp (275 nm).

12% hydrofluoric acid solution is dripped onto the substrate with the glass side facing up in such a manner that no hydrofluoric acid comes in contact with the PEG hydrogel over the edge of the glass. After a few hours the glass separates from the hydrogel film.

The hydrogel is washed in MQ water several times and pre-served in the water.

Example 3

Transfer of Gold Structures into a PEG Tube

Suspend the glass fiber with a diameter of 50-150 µm and structured with gold nanostructures for 3 hours in propenethiol vapor. The fiber is subsequently placed in a drop of PEG-DA with photoinitiator Irgacure 2959. After a 45-minute UV irradiation under nitrogen the glass fiber is held with one end in a 12% hydrofluoric acid solution in such a manner that approximately two thirds of the solidified PEG drop still extends out of the acid. As soon as the hydrofluoric acid, which rises upward along the glass fiber inside the PEG drop, reaches the upper end of the PEG drop, the fiber is decimated in its diameter in such a manner that it can be withdrawn from the PEG drop and leaves the gold structures behind inside the tube produced.

Example 4

Production of a Biofunctionalized PEG Matrix with Gold Nanostructures 1 mg 2-carboxyethylacrylate is dissolved in 500 ml PEG-DA 700. The solution is used in accordance with example 2 for transferring gold structures. After the polymerization and the transfer of the gold structures onto the PEG the carboxyl groups can be transferred in N-hydroxy-succinimide ester. This takes place by transferring the substrates into a 1% solution of N-hydroxy-succinimides in a HEPES buffer (pH 7.3). A following binding of tris-(carboxymethyl) amine (NTA) in dried DMSO and the complexing with nickel makes possible the binding of any proteins via histidine. After the binding of NTA and before the nickel complexing the gold structures can be functionalized via a thiol group with a bioactive molecule, e.g., RGD.

The invention claimed is:

1. A method for the production of a surface-structured substrate, comprising the steps:
   (i) providing a first substrate that is nanostructured on at least one surface with inorganic nanoclusters,
   (ii) applying a substrate material for a second substrate different from the first substrate on the nanostructured surface of the first substrate, and
   (iii) separating the first substrate from the second substrate and the inorganic nanoclusters, such that the second substrate nanostructured with nanoclusters is obtained; wherein the nanostructures are at least partially embedded in the second substrate and at least partially exposed.

2. The method according to claim 1, wherein the applying of the second substrate material takes place in step (ii) by a process selected from the group consisting of thermal evaporation, electron beam evaporation, sputtering and electrochemical deposition.

3. The method according to claim 2, wherein the second substrate material is selected from the group consisting of Si, C, zinc oxide, Cr, indium oxide, Cu, hexadecafluoro-phthalocyanin (F16CuPc), indium arsenide, gallium arsenide, aluminum oxide, calcium fluoride and magnesium fluoride.

4. A method for the production of a polymeric surface-structured substrate, comprising the steps:
   (a) providing a first substrate that is nanostructured on at least one surface with inorganic nanoclusters,
   (b) applying a hardenable substrate material for a second substrate different from the first substrate on the nanostructured surface of the first substrate, the hardenable substrate material being selected from the group consisting of an organic cross-linkable polymer, a non-cross-linkable polymer, a resin, an organic polymerizable and cross-linkable oligomer, an organic polymerizable oligomer, a cross-linkable oligomer, an organic polymerizable polymer precursor, and mixtures thereof,
   (c) hardening the substrate material for the second substrate, and
   (d) separating the first substrate from the second substrate and the inorganic nanoclusters, such that the second substrate nanostructured with nanoclusters is obtained; wherein the nanostructures are at least partially embedded in the second substrate and at least partially exposed.

5. The method according to claim 4, in which a step of immobilizing a binding molecule is carried out between step (a) and step (b).

6. The method according to claim 5, in which the binding molecule is selected from the group consisting of propenethiol, mercaptopolyethylene-glycolacrylate, polyethyleneglycoldithiol, cysteamine with acryloylchloride, alkylthioglycolate and amino-1-alkylthiol, wherein alkyl designates a straight or branched, saturated or unsaturated hydrocarbon with 1 to 24 carbon atoms.

7. The method according to claim 5, in which the binding molecules are receptors of a cell.

8. A method for the production of a polymeric surface-structured substrate, comprising the steps:
   (a') taking up a polymer in a suitable solvent under formation of a dissolved core shell polymer system,
   (b') charging at least one part of the cores of the core shell polymer system with at least one, same or different metal compounds that form nanoclusters,
   (c') applying the core shell polymer system obtained in step (b') as a film onto at least one side of a substrate in such a manner that the core shell polymer system is arranged in a regular structure in the film,
   (d') partially removing the polymer of the core shell polymer system applied on the substrate in step (c'), as a result of which the nanoclusters are at least partially embedded in the polymer but no longer completely surrounded by the polymer, and
   (e') separating the substrate from the film obtained in step (d'), as a result of which a polymeric film nanostructured with nanoclusters is obtained.

9. The method according to claim 8, in which the first substrate from (a') has a three-dimensional form.

10. The method according to claim 8, in which the inorganic clusters are Au clusters.

11. The method according to claim 8, in which the inorganic nanoclusters are arranged in a structured manner with a distance of 1 nm to 300 µm.

12. A substrate with a structured surface having nanostructures that are at least partially embedded and at least partially exposed, obtainable by a method according to claim 8.

13. The method of claim 8, further comprising applying the substrate on a stent material.

14. The method of claim 8, further comprising adhering cells to the substrate.

15. The method of claim 8, further comprising binding biologically active molecules to the substrate for the imitation, manipulation, examination and quantification of biological systems.

16. The method of claim 8, further comprising producing components from the substrate, the components being selected from the group consisting of: electronic components, optical components and chemical sensors.

17. The method according to claim 2, wherein the second substrate material is selected from a group consisting of a conductor and a semiconductor.

18. The method according to claim 1, in which the first substrate from step (i) has a three-dimensional form.

19. The method according to claim 1, in which the inorganic nanoclusters are Au clusters.

20. The method according to claim 1, in which the inorganic nanoclusters are arranged in a structured manner with a distance of 1 nm to 300 µm.

21. A substrate with a structured surface having nanostructures that are at least partially embedded and at least partially exposed, obtainable by a method according to claim 1.

22. The method of claim 1, further comprising applying the second substrate on a stent material.

23. The method of claim 1, further comprising applying the second substrate on an implant material.

24. The method of claim 1, further comprising adhering cells to the second substrate.

25. The method of claim 1, further comprising adhering viruses to the second substrate.

26. The method of claim 1, further comprising adhering bacteria to the second substrate.

27. The method of claim 1, further comprising binding biologically active molecules to the second substrate for the imitation, manipulation, examination and quantification of biological systems.

28. The method of claim 1, further comprising producing components from the second substrate, the components being selected from a group consisting of: electronic components, optical components and chemical sensors.

29. The method according to claim 4, in which the first substrate from step (a) has a three-dimensional form.

30. The method according to claim 4, in which the inorganic nanoclusters are Au clusters.

31. The method according to claim 4, in which the inorganic nanoclusters are arranged in a structured manner with a distance of 1 nm to 300 µm.

32. A substrate with a structured surface having nanoclusters that are at least partially embedded and at least partially exposed, obtainable by a method according to claim 4.

33. The method of claim 4, further comprising applying the second substrate on a stent material.

34. The method of claim 4, further comprising applying the second substrate on an implant material.

35. The method of claim 4, further comprising adhering cells to the second substrate according to claim 32 for the adhesion of cells.

36. The method of claim 4, further comprising adhering viruses to the second substrate.

37. The method of claim 4, further comprising adhering bacteria to the second substrate.

38. The method of claim 4, further comprising binding biologically active molecules to the second substrate for the imitation, manipulation, examination and quantification of biological systems.

39. The method of claim 4, further comprising producing components from the second substrate, the components being selected from a group consisting of: electronic components, optical components, and chemical sensors.

40. The method of claim 8, further comprising applying the substrate on an implant material.

41. The method of claim 8, further comprising adhering viruses to the substrate.

42. The method of claim 8, further comprising adhering bacteria to the substrate.

* * * * *